US012566178B2

(12) United States Patent
Bettoun et al.

(10) Patent No.: US 12,566,178 B2
(45) Date of Patent: Mar. 3, 2026

(54) METHODS OF QUANTIFYING FRATAXIN AND FRATAXIN FUSION PROTEINS

(71) Applicants: Larimar Therapeutics, Inc., Bala Cynwyd, PA (US); The United States of America, as represented by the Secretary, Department of Health and Human Services, Bethesda, MD (US)

(72) Inventors: Joan David Bettoun, Elkins Park, PA (US); Erik Johan Wagner, Sterling, VA (US); Xin Xu, Potomac, MD (US); Jean-Nicholas Mess, Laval (CA); Amy Qiu Wang, Poolesville, MD (US)

(73) Assignees: Larimar Therapeutics, Inc., Bala Cynwyd, PA (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 992 days.

(21) Appl. No.: 17/631,414

(22) PCT Filed: Jul. 29, 2020

(86) PCT No.: PCT/US2020/044118
§ 371 (c)(1),
(2) Date: Jan. 28, 2022

(87) PCT Pub. No.: WO2021/021964
PCT Pub. Date: Feb. 4, 2021

(65) Prior Publication Data
US 2022/0276258 A1 Sep. 1, 2022

Related U.S. Application Data

(60) Provisional application No. 62/936,293, filed on Nov. 15, 2019, provisional application No. 62/880,068, filed on Jul. 29, 2019.

(51) Int. Cl.
*G01N 31/00* (2006.01)
*G01N 33/53* (2006.01)
*G01N 33/68* (2006.01)

(52) U.S. Cl.
CPC ................................ *G01N 33/6848* (2013.01)

(58) Field of Classification Search
None
See application file for complete search history.

(56) References Cited

U.S. PATENT DOCUMENTS

| | | | |
|---|---|---|---|
| 8,283,444 | B2 | 10/2012 | Payne |
| 11,459,363 | B2 | 10/2022 | Payne |
| 2005/0169904 | A1 | 8/2005 | Payne |
| 2012/0196328 | A1 | 8/2012 | Liu et al. |
| 2014/0135275 | A1 | 5/2014 | Keefe et al. |
| 2014/0187606 | A1 | 7/2014 | Collard et al. |
| 2014/0308262 | A1 | 10/2014 | Lorberboum-Galski |
| 2015/0132769 | A1 | 5/2015 | Payne et al. |
| 2016/0060605 | A1 | 3/2016 | Testi |
| 2017/0320968 | A1 | 11/2017 | Tremblay et al. |
| 2017/0327847 | A1 | 11/2017 | Ghadessy et al. |
| 2018/0333386 | A1 | 11/2018 | Cortopassi et al. |
| 2019/0002876 | A1 | 1/2019 | Corey et al. |
| 2019/0076429 | A1 | 3/2019 | Rufini et al. |
| 2020/0377951 | A1 | 12/2020 | Bettoun |
| 2021/0156874 | A1 | 5/2021 | Bettoun |
| 2021/0355177 | A1 | 11/2021 | Bettoun et al. |
| 2021/0363205 | A1 | 11/2021 | Bettoun |
| 2022/0193190 | A1 | 6/2022 | Boyle et al. |
| 2022/0378869 | A1 | 12/2022 | Bettoun |
| 2023/0242600 | A1 | 8/2023 | Payne |
| 2024/0343766 | A1 | 10/2024 | Bettoun |
| 2024/0391966 | A1 | 11/2024 | Payne |
| 2025/0085297 | A1 | 3/2025 | Bettoun |

FOREIGN PATENT DOCUMENTS

| | | |
|---|---|---|
| CA | 2649538 A1 | 11/2007 |
| CA | 3147742 A1 | 1/2021 |
| CN | 103620036 A | 3/2014 |
| CN | 114450309 A | 5/2022 |
| EP | 1752536 A1 | 2/2007 |
| EP | 2750686 A1 | 7/2014 |
| JP | 2016-520557 A | 7/2016 |
| JP | 2023-518996 A | 5/2023 |
| WO | 2004/032863 A2 | 4/2004 |
| WO | 2005/116204 A1 | 12/2005 |
| WO | 2006/108581 A2 | 10/2006 |
| WO | 2007/124082 A2 | 11/2007 |
| WO | 2011/103536 A1 | 8/2011 |
| WO | 2012/014083 A2 | 2/2012 |
| WO | 2012/050402 A2 | 4/2012 |
| WO | 2012/174452 A1 | 12/2012 |

(Continued)

OTHER PUBLICATIONS

Gonzalez et al. (Drug Metabolism and Pharmacokinetics, 35(1), S38, Jan. 2020) Meeting date Jul. 28, 2019 (Year: 2019).*
Scultz et al., Off-target effects dominate a large-scale RNAi screen for modulators of the TGF-ß pathway and reveal microRNA regulation of TGFBR2. Silence. Mar. 14, 2011;2:3, 20 pages.
International Search Report and Written Opinion for Application No. PCT/US2020/044400, dated Oct. 22, 2020, 19 pages.
Agrawal et al., CPPsite 2.0: a repository of experimentally validated cell-penetrating peptides. Nucleic Acids Res. Jan. 4, 2016;44(D1):D1098-103.
Chauhan et al., The taming of the cell penetrating domain of the HIV Tat: myths and realities. J Control Release. Feb. 12, 2007;117(2):148-62.
CPPsite2.0, Welcome to Statistics page CPPsite 2.0. Retrieved online at: <https://webs.iiitd.edu.in/raghava/cppsite/stats 1.php.> 2 pages, Retrieved Jan. 2, 2025.

(Continued)

*Primary Examiner* — Lisa V Cook
(74) *Attorney, Agent, or Firm* — McCarter & English, LLP; Jill Mello; Yelena Margolin

(57) ABSTRACT

The present disclosure provides methods for determining the amount of FXN or FXN fusion protein in a sample, e.g., a tissue sample, by using mass spectrometry.

18 Claims, 4 Drawing Sheets

Specification includes a Sequence Listing.

(56) References Cited

FOREIGN PATENT DOCUMENTS

| | | |
|---|---|---|
| WO | 2013/036596 A2 | 3/2013 |
| WO | 2013/071440 A1 | 5/2013 |
| WO | 2016/115632 A1 | 7/2016 |
| WO | 2016/119856 A1 | 8/2016 |
| WO | 2016/172659 A1 | 10/2016 |
| WO | 2017/161354 A1 | 9/2017 |
| WO | 2017/165167 A1 | 9/2017 |
| WO | 2021/011929 A1 | 1/2021 |
| WO | 2021/021931 A1 | 2/2021 |
| WO | 2021/195597 A2 | 9/2021 |

OTHER PUBLICATIONS

Guo et al., Protein tolerance to random amino acid change. Proc Natl Acad Sci U S A. Jun. 22, 2004;101(25):9205-10.

Jiang et al., Frataxin and Friedreich's Ataxia. Chinese Journal of Neuroscience. Oct. 31, 2003;36(5):385-387.

Kuramoto et al., A mutation in the gene encoding mitochondrial $Mg^2+$ channel MRS2 results in demyelination in the rat. PLoS Genet. Jan. 6, 2011;7(1):e1001262, 10 pages.

Lake et al., Leigh syndrome: One disorder, more than 75 monogenic causes. Ann Neurol. Feb. 2016;79(2):190-203.

Lazaropoulos et al., Frataxin levels in peripheral tissue in Friedreich ataxia. Ann Clin Transl Neurol. Aug. 2015;2(8):831-42.

Lowe, Not AlphaFold's Fault. In the pipeline. 6 pages. Sep. 7, 2022.

Massodi et al., Application of thermally responsive elastin-like polypeptide fused to a lactoferrin-derived peptide for treatment of pancreatic cancer. Molecules. Jun. 4, 2009;14(6):1999-2015.

Mathis et al., The ataxic neuropathies. J Neurol. Oct. 2021;268(10):3675-3689.

Scopes, Enzyme Activity and Assays. Encyclopedia of Life Sciences. pp. 1-6, (2002).

Stauber et al., Intracellular trafficking and interactions of the HIV-1 Tat protein. Virology. Dec. 5, 1998;252(1):126-36.

Sutton et al., DIRAS3-Derived Peptide Inhibits Autophagy in Ovarian Cancer Cells by Binding to Beclin1. Cancers (Basel). Apr. 18, 2019;11(4):557, 14 pages.

Vitte et al., Intracellular delivery of peptides via association with ubiquitin or SUMO-1 coupled to protein transduction domains. BMC Biotechnol. Feb. 29, 2008;8:24, 11 pages.

Yampolsky et al., The exchangeability of amino acids in proteins. Genetics. Aug. 2005;170(4):1459-72.

International Preliminary Report on Patentability for Application No. PCT/US2020/044069, dated Feb. 10, 2022, 9 pages.

International Search Report and Written Opinion for Application No. PCT/US2020/044118, dated Feb. 22, 2021, 20 pages.

International Search Report and Written Opinion for Application No. PCT/US2021/024534, dated Oct. 6, 2021, 15 pages.

U.S. Appl. No. 16/942,276, filed Jul. 29, 2020, U.S. Pat. No. 11,459,363, Issued.

U.S. Appl. No. 17/900,450, filed Aug. 31, 2022, 2023-0242600, Published.

U.S. Appl. No. 17/627,638, filed Jan. 14, 2022, 2022-0378869, Published.

U.S. Appl. No. 17/105,149, filed Nov. 25, 2020, 2021-0156874, Published.

U.S. Appl. No. 17/246,549, filed Apr. 30, 2021, 2021-0363205, Published.

U.S. Appl. No. 17/549,770, filed Dec. 13, 2021, 2022-0193190, Published.

Abrahao et al., Milestones in Friedreich ataxia: more than a century and still learning. Neurogenetics. Jul. 2015;16(3):151-60.

Belbellaa et al., High Levels of Frataxin Overexpression Lead to Mitochondrial and Cardiac Toxicity in Mouse Models. Mol Ther Methods Clin Dev. Sep. 1, 2020;19:120-138.

Bencze et al., The structure and function of frataxin. Crit Rev Biochem Mol Biol. Sep.-Oct. 2006;41(5):269-91.

Bou-Abdallah et al., Iron binding and oxidation kinetics in frataxin CyaY of Escherichia coli. J Mol Biol. Aug. 6, 2004;341(2):605-15.

Correia et al., Conformational stability of human frataxin and effect of Friedreich's ataxia-related mutations on protein folding. Biochem J. Sep. 15, 2006;398(3):605-11.

European Medicines Agency, Public summary of opinion on orphan designation: Human Frataxin fused to TAT cell-penetrating peptide for the treatment of Friedreich's ataxia. Nov. 13, 2020. One page.

Guo et al., Liquid Chromatography-High Resolution Mass Spectrometry Analysis of Platelet Frataxin as a Protein Biomarker for the Rare Disease Friedreich's Ataxia. Anal Chem. Feb. 6, 2018;90(3):2216-2223.

Han et al., Mechanisms of iron and copper-frataxin interactions. Metallomics. Aug. 16, 2017;9(8):1073-85.

Hayashi et al., Oxidative stress in inherited mitochondrial diseases. Free Radic Biol Med. Nov. 2015;88(Pt A):10-7.

Khdour et al., Lipophilic methylene blue analogues enhance mitochondrial function and increase frataxin levels in a cellular model of Friedreich's ataxia. Bioorg Med Chem. Jul. 23, 2018;26(12):3359-3369.

Lu et al., Frataxin deficiency induces Schwann cell inflammation and death. Biochim Biophys Acta. Nov. 2009;1792(11):1052-61.

Mastrangelo, Clinical approach to neurodegenerative disorders in childhood: an updated overview. Acta Neurol Belg. Dec. 2019;119(4):511-21.

Pandolfo, Drug Insight: antioxidant therapy in inherited ataxias. Nat Clin Pract Neurol. Feb. 2008;4(2):86-96.

Raynal et al., Quality assessment and optimization of purified protein samples: why and how? Microb Cell Fact. Dec. 30, 2014;13:180, 10 pages.

Sasarman et al., Tissue-specific responses to the LRPPRC founder mutation in French Canadian Leigh Syndrome. Hum Mol Genet. Jan. 15, 2015;24(2):480-91.

Shoichet et al., Frataxin promotes antioxidant defense in a thiol-dependent manner resulting in diminished malignant transformation in vitro. Hum Mol Genet. Apr. 1, 2002;11(7):815-21.

Vyas et al., A TAT-frataxin fusion protein increases lifespan and cardiac function in a conditional Friedreich's ataxia mouse model. Hum Mol Genet. Mar. 15, 2012;21(6):1230-47.

International Search Report and Written Opinion for Application No. PCT/US2020/044069, dated Oct. 28, 2020, 12 pages.

International Search Report and Written Opinion for Application No. PCT/US2020/062355, dated Mar. 12, 2021, 13 pages.

International Search Report and Written Opinion for Application No. PCT/US2021/030348, dated Aug. 9, 2021, 24 pages.

International Search Report and Written Opinion for Application No. PCT/US2021/063163, dated Apr. 11, 2022, 16 pages.

Internatonal Search Report and Written Opinion for Application No. PCT/US2020/042683, dated Nov. 4, 2020, 12 pages.

* cited by examiner

Skin Biopsies
8 mm skin punches were finely minced with a scalpel and homogenized in RIPA buffer using a FastPrep-96 and sonication.

Buccal Cells
Cells scraped with a buccal swab (Isohelix SK-2S) were extracted and lysed by incubation in RIPA buffer, vortexing and sonication.

Platelets
Blood samples were collected in 8.5mL ACD tubes, the platelets were isolated by centrifugation and lysed in RIPA buffer by vortexing and sonication.

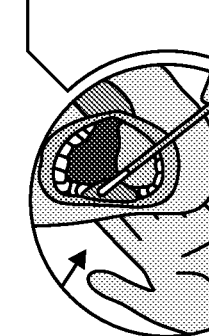
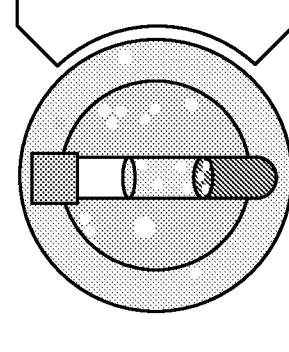

FIG. 1

METHODS OF QUANTIFYING FRATAXIN AND FRATAXIN FUSION PROTEINS

RELATED APPLICATIONS

This application is a 35 U.S.C. § 371 national stage filing of International Application No. PCT/US2020/044118, filed on Jul. 29, 2020, which claims priority to U.S. Provisional Patent Application No. 62/880,068, filed on Jul. 29, 2019 and U.S. Provisional Patent Application No. 62/936,293, filed on Nov. 15, 2019. The entire contents of each of the foregoing applications are hereby incorporated herein by reference.

SEQUENCE LISTING

The instant application contains a Sequence Listing which has been submitted electronically in ASCII format and is hereby incorporated by reference in its entirety. Said ASCII copy, created on Jul. 28, 2020, is named 130197-00920_SL.txt and is 9,786 bytes in size.

INTRODUCTION

Friedreich's Ataxia (FRDA) is a rare genetic, progressive neurodegenerative disorder caused by a mutation in a gene encoding frataxin (FXN). FXN is an essential and phylogenetically conserved protein that is found in cells throughout the body, with the highest levels in the heart, spinal cord, liver, pancreas, and skeletal muscle. FXN is encoded in the nucleus, expressed in the cytoplasm and imported into the mitochondria where it is processed to the mature form. In humans, the 210-amino acid full-length hFXN (hFXN$_{1-210}$, 23.1 kDa) contains a typical mitochondrial targeting sequence (MTS) at the amino terminus that is processed in a 2-step cleavage by the mitochondrial matrix processing peptidase (MPP) as it is imported into the mitochondrial matrix. The resulting protein is a 130-amino acid, 14.2 kDa mature hFXN protein (hFXN$_{81-210}$).

TAT-GG-FXN is a 24.9 kDa fusion protein currently under investigation as an FXN replacement therapy to restore functional levels of FXN in the mitochondria of FRDA patients. TAT-GG-FXN includes the HIV-TAT peptide linked to the N-terminus of the full-length hFXN protein. The mechanism of action of TAT-GG-FXN relies on the cell-penetrating ability of the HIV-TAT peptide to deliver the TAT-GG-FXN into cells and the subsequent processing into mature hFXN after translocation into the mitochondria. TAT-GG-FXN (SEQ ID NO: 11) is described in U.S. Provisional Patent Application No. 62/891,029, the entire contents of each of which are hereby incorporated herein by reference.

To facilitate development of FXN replacement therapies, new reliable methods are needed to accurately and precisely measure level of FXN and FXN fusion proteins in various biological fluids and tissues of a subject.

SUMMARY OF THE INVENTION

In one aspect, the present disclosure provides a method for determining the amount of unprocessed frataxin (FXN) fusion protein in a sample, said method comprising determining the amount of a peptide in said sample by using mass spectrometry (MS), wherein said peptide comprises, or consists of, the amino acid sequence GGMWTLGR (SEQ ID NO: 12); and wherein said unprocessed FXN fusion protein comprises, or consists of, from N-terminus to C-terminus, a cell penetrating peptide (CPP); a mitochondrial targeting sequence (MTS) comprising, or consisting of, SEQ ID NO: 3; and FXN comprising, or consisting of, SEQ ID NO: 2.

In one embodiment, said sample is obtained from a subject being administered the unprocessed FXN fusion protein.

In one embodiment, said CPP comprises, or consists of, HIV-TAT (SEQ ID NO: 4) or HIV-TAT+M (SEQ ID NO: 15).

In one embodiment, said unprocessed FXN fusion protein is TAT-GG-FXN (SEQ ID NO: 11).

In one embodiment, said method comprises purifying by immunocapture the unprocessed FXN fusion protein from said sample prior to MS.

In one embodiment, said method comprises the following steps:

a) purifying by immunocapture the unprocessed FXN fusion protein from said sample, thereby obtaining immunocaptured complexes comprising the unprocessed FXN fusion protein;

b) subjecting said immunocaptured complexes comprising the unprocessed FXN fusion protein to digestion by trypsin, thereby producing the peptide comprising, or consisting of, SEQ ID NO: 12; and c) determining the amount of the peptide comprising, or consisting of, SEQ ID NO: 12 by liquid chromatography and tandem mass spectrometry (LC/MS-MS).

In one embodiment, in part c) the liquid chromatography (LC) comprises reversed-phase chromatography.

In one embodiment, tandem mass spectrometry (MS-MS) comprises monitoring the transition 439.2→632.3.

In one embodiment, the tandem mass spectrometry (MS-MS) comprises monitoring the transition 439.2→446.3.

In one embodiment, the immunocapture is carried out using a binding protein comprising an antigen binding domain that specifically binds to the FXN fusion protein.

In one embodiment, said binding protein specifically binds to the FXN present in the FXN fusion protein.

In one embodiment, said binding protein specifically binds to the CPP present in the FXN fusion protein.

In one embodiment, the FXN fusion protein comprises HIV-TAT (SEQ ID NO: 4) or HIV-TAT+M (SEQ ID NO: 15) and wherein said binding protein specifically binds to the HIV-TAT.

In one embodiment, the sample is a tissue sample.

In one embodiment, the tissue sample comprises a buccal swab.

In one embodiment, the tissue sample comprises a skin biopsy.

In one embodiment, the sample is derived from the blood of the subject.

In one embodiment, the sample comprises platelets.

In one embodiment, the sample is a plasma sample.

In one embodiment, the method has a precision as measured by % coefficient of variation (% CV) of about 20% or less.

In one embodiment, the method has a precision as measured by % CV of about 15% or less, about 14% or less, about 13% or less, about 12% or less, about 11% or less, about 10% or less, about 9% or less, about 8% or less, about 7% or less, about 6% or less, about 5% or less, about 4% or less, about 3% or less, about 2% or less or about 1% or less.

In one embodiment, the method has an accuracy of about 80% to about 120%.

In one embodiment, the method is linear for concentration of unprocessed FXN fusion protein ranging from about 0.250 ng/mL to about 25.000 ng/mL.

In another aspect, the present disclosure provides a method of monitoring processing of unprocessed FXN fusion protein in a sample, said method comprising:

obtaining at least two temporally separated samples from said subject; and determining the amount of unprocessed FXN fusion protein in said temporally separated samples using the methods of the present disclosure.

In one embodiment, the sample is derived from a subject being administered the unprocessed FXN fusion protein.

In yet another aspect, the present disclosure provides a method of adjusting a dosing schedule for administering unprocessed FXN fusion protein, said method comprising:

obtaining at least two temporally separated samples from the subject being administered unprocessed FXN fusion protein;

determining the amount of unprocessed FXN fusion protein in said temporally separated samples using the methods of the present disclosure; and adjusting the dose of unprocessed FXN fusion protein being administered to the subject and/or dosing frequency of the unprocessed FXN fusion protein being administered to the subject based on the temporal changes in the amount of unprocessed FXN fusion protein observed in the subject.

In still another aspect, the present disclosure provides a method for determining the amount of unprocessed FXN fusion protein, e.g., TAT-GG-FXN (SEQ ID NO: 11), in a sample, said method comprising determining the amount of at least one peptide in said sample by using MS, wherein said at least one peptide is selected from the group consisting of:

a) a peptide comprising, or consisting of, the amino acid sequence SGTLGHPGSLDETTYER (SEQ ID NO: 13); and b) a peptide comprising, or consisting of, the amino acid sequence LGGDLGTYVINK (SEQ ID NO: 14);

wherein said method comprises purifying by immunocapture the unprocessed TAT-GG-FXN from said sample prior to MS;

wherein said immunocapture is carried out using a binding protein comprising an antigen binding domain, wherein said binding protein is capable of binding a TAT protein transduction domain.

In one embodiment, said sample is obtained from a subject being administered the unprocessed TAT-GG-FXN (SEQ NO: 11).

In one embodiment, said method comprises the following steps:

a) purifying by immunocapture the unprocessed FXN fusion protein, e.g., TAT-GG-FXN from said sample, thereby obtaining immunocaptured complexes comprising the unprocessed FXN fusion protein, e.g., TAT-GG-FXN;

b) subjecting said immunocaptured complexes comprising the unprocessed FXN fusion protein, e.g., TAT-GG-FXN to digestion by a protease, e.g., trypsin, thereby producing the peptide comprising, or consisting of, SEQ ID NO: 13 and/or the peptide comprising, or consisting of, SEQ ID NO: 14; and c) determining the amount of the peptide comprising, or consisting of, SEQ ID NO: 13 and/or the peptide comprising, or consisting of, SEQ ID NO: 14 by LC/MS-MS.

In one embodiment, in part c) the LC comprises reversed-phase chromatography.

In one embodiment, the MS-MS comprises monitoring the transition 607.3→669.3 for the peptide comprising, or consisting of, SEQ ID NO: 13 and the transition 625.3→794.4 for the peptide comprising, or consisting of, SEQ ID NO: 14.

In one embodiment, the sample is a tissue sample.

In one embodiment, the tissue sample comprises a buccal swab.

In one embodiment, the tissue sample comprises a skin biopsy.

In one embodiment, the sample is derived from the blood of the subject.

In one embodiment, the sample comprises platelets.

In one embodiment, the sample is a plasma sample.

In one embodiment, the method has a precision as measured by % coefficient of variation (% CV) of 20% or less;

In one embodiment, the method has an accuracy of about 80% to about 120%.

In one embodiment, the method is linear for concentrations of unprocessed TAT-GG-FXN ranging from 0.250 ng/mL to 25.000 ng/mL.

In another aspect, the present disclosure provides a method for determining the amount of FXN in a tissue sample, said method comprising determining the amount of at least one peptide derived from said FXN in said sample by using MS, wherein said at least one peptide is selected from the group consisting of:

a) a peptide comprising, or consisting of, the amino acid sequence SGTLGHPGSLDETTYER (SEQ ID NO: 13); and b) a peptide comprising, or consisting of, the amino acid sequence LGGDLGTYVINK (SEQ ID NO: 14);

wherein the method is characterized by at least one of the following:

the method has a precision as measured by % coefficient of variation (% CV) of 20% or less; and the method has an accuracy of about 80% to about 120%.

In one embodiment, said sample is obtained from a subject.

In one embodiment, said subject is being administered unprocessed FXN fusion protein.

In one embodiment, said unprocessed FXN fusion protein comprises, or consists of, from N-terminus to C-terminus, a cell penetrating peptide (CPP), a mitochondrial targeting sequence (MTS) of SEQ ID NO: 3 and FXN.

In one embodiment, said CPP comprises, or consists of, HIV-TAT (SEQ ID NO: 4) or HIV-TAT+M (SEQ ID NO: 15).

In one embodiment, said unprocessed FXN fusion protein is TAT-GG-FXN (SEQ ID NO: 11).

In one embodiment, said method comprises purifying by immunocapture the FXN from said sample prior to MS.

In one embodiment, said method comprises the following steps:

a) purifying by immunocapture the FXN from said sample, thereby obtaining immunocaptured complexes comprising FXN;

b) subjecting said immunocaptured complexes compris-
ing FXN to digestion by a protease, e.g., trypsin,
thereby producing the peptide comprising, or consist-
ing of, SEQ ID NO: 13 and/or the peptide comprising,
or consisting of, SEQ ID NO: 14; and c) determining the amount of at least one peptide selected
from the group consisting of the peptide comprising, or
consisting of, SEQ ID NO: 13 and/or the peptide
comprising, or consisting of, SEQ ID NO: 14 by
LC/MS-MS.

In one embodiment, in part c) the LC comprises reversed-
phase chromatography.

In one embodiment, the tandem mass spectrometry (MS-
MS) comprises monitoring the transition $607.3 \rightarrow 669.3$ for
the peptide comprising, or consisting of, SEQ ID NO: 13 and
the transition $625.3 \rightarrow 794.4$ for the peptide comprising, or
consisting of, SEQ ID NO: 14.

In one embodiment, the immunocapture is carried out
using a binding protein comprising an antigen binding
domain that specifically binds FXN.

In one embodiment, said FXN is a part of an FXN fusion
protein also comprising HIV-TAT (SEQ ID NO: 4) or
HIV-TAT+M (SEQ ID NO: 15) and wherein said binding
protein specifically binds the HIV-TAT.

In one embodiment, the tissue sample comprises a buccal
swab.

In one embodiment, the tissue sample comprises a skin
biopsy.

In another aspect, the present disclosure provides a
method for determining the amount of FXN in a skin
sample, said method comprising determining the amount of
at least one peptide derived from said FXN in said skin
sample by using MS, wherein said at least one peptide is selected from the
group consisting of:

a) a peptide comprising, or consisting of, the amino
acid sequence GGMWTLGR (SEQ ID NO: 12);

b) a peptide comprising, or consisting of, the amino
acid sequence SGTLGHPGSLDETTYER (SEQ ID
NO: 13); and c) a peptide comprising, or consisting of, the amino
acid sequence LGGDLGTYVINK (SEQ ID NO:
14).

In one embodiment, said skin sample is obtained from a
subject.

In one embodiment, said subject is being administered
unprocessed FXN fusion protein.

In one embodiment, said unprocessed FXN fusion protein
comprises, or consists of, from N-terminus to C-terminus, a
cell penetrating peptide (CPP), a mitochondrial targeting
sequence (MTS) of SEQ ID NO: 3 and FXN, e.g., FXN of
SEQ ID NO: 2.

In one embodiment, said CPP comprises, or consists of,
HIV-TAT (SEQ ID NO: 4) or HIV-TAT+M (SEQ ID NO:
15).

In one embodiment, said unprocessed FXN fusion protein
is TAT-GG-FXN (SEQ ID NO: 11).

In one embodiment, said method comprises purifying by
immunocapture the FXN from said skin sample prior to MS.

In one embodiment, said method comprises the following
steps:

a) purifying by immunocapture FXN from said skin
sample, thereby obtaining immunocaptured complexes
comprising FXN;

b) subjecting said immunocaptured complexes compris-
ing FXN to digestion by a protease, e.g., trypsin,
thereby producing the peptide comprising, or consisting of, SEQ ID NO: 12 and/or the peptide comprising,
or consisting of, SEQ ID NO: 13 and/or the peptide
comprising, or consisting of, SEQ ID NO: 14; and c) determining the amount of at least one peptide selected
from the group consisting of the peptide comprising, or
consisting of, SEQ ID NO: 12 and/or the peptide
comprising, or consisting of, SEQ ID NO: 13 and/or the
peptide comprising, or consisting of, SEQ ID NO: 14
by LC/MS-MS.

In one embodiment, said immunocapture is carried out
using a binding protein comprising an antigen binding
domain that specifically binds FXN.

In one embodiment, said FXN is a part of an FXN fusion
protein also comprising HIV-TAT (SEQ ID NO: 4) or
HIV-TAT+M (SEQ ID NO: 15) and wherein said binding
protein specifically binds the HIV-TAT.

BRIEF DESCRIPTION OF THE DRAWINGS

FIG. 1 is an illustration of the procedure used for the
preparation of biological samples for quantifying TAT-GG-
FXN (SEQ ID NO: 11).

FIG. 2 discloses SEQ ID NOS 12-14, respectively, in
order of appearance.

DETAILED DESCRIPTION OF THE INVENTION

Figure 2:
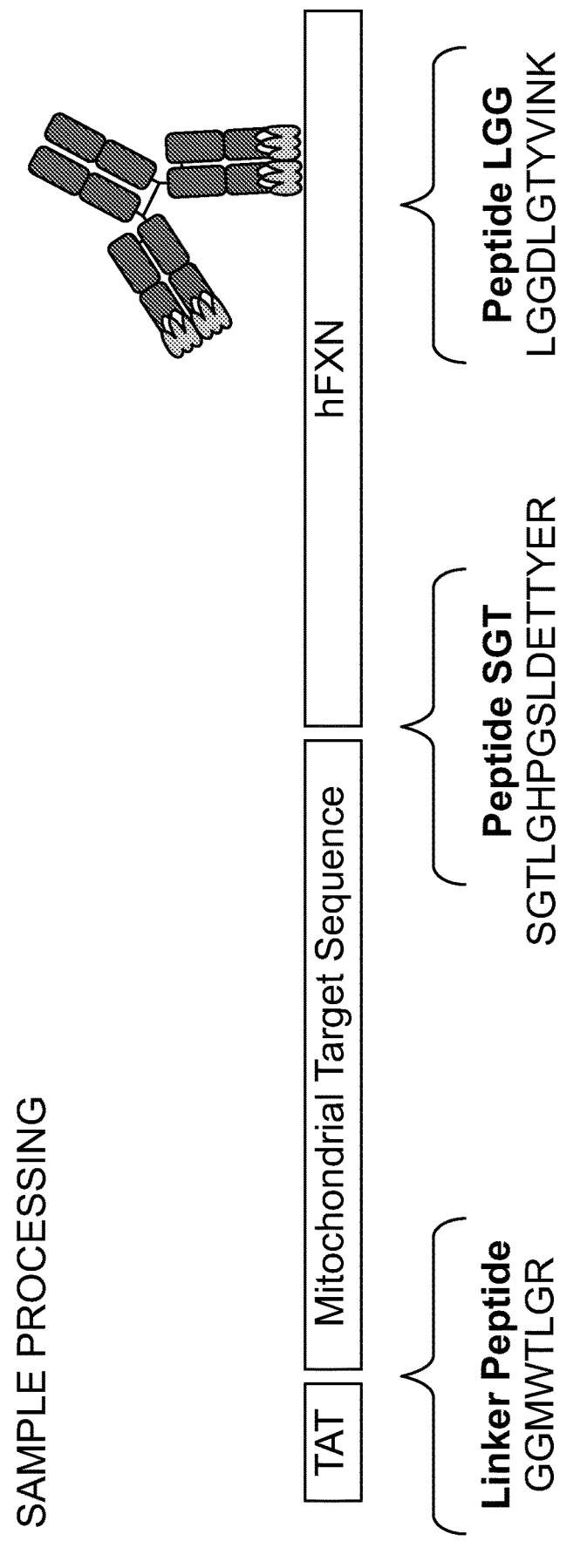
FIG. 2 is an illustration of sample processing for hybrid
LC-MS/MS analysis.

The present disclosure provides methods for determining
the amount of frataxin (FXN) or an FXN fusion protein in
a sample using mass spectrometry (MS). FXN is a protein
which is associated with the disorder Friedreich's Ataxia
(FRDA). FRDA is a genetic, progressive neurodegenerative
disorder caused by a mutation in a gene encoding FXN.
Methods of the present disclosure may be used, e.g., to
monitor the levels of FXN in a subject, e.g., a subject who
is being administered FXN as a protein replacement therapy
for treating FRDA. Methods of the present invention may
also be used to monitor processing of an FXN fusion protein,
e.g., TAT-GG-FXN (SEQ ID NO: 11), after the FXN fusion
protein is added to an in vitro sample or is administered to
a subject. Methods of the present disclosure may also be
used to monitor levels of FXN or an FXN fusion protein in
a subject, e.g., subject who is being administered an FXN
fusion protein, and to adjust the dose or the dosing frequency
of the FXN fusion protein.

FXN and FXN Fusion Protein

FXN is an essential and phylogenetically conserved pro-
tein that is found in cells throughout the body, with the
highest levels in the heart, spinal cord, liver, pancreas, and
skeletal muscle. FXN is encoded in the nucleus, expressed
in the cytoplasm and imported into the mitochondria where
it is processed to the mature form. In humans, the 210-amino
acid full-length hFXN (hFXN$_{1-210}$, 23.1 kDa) contains a
typical mitochondrial targeting sequence (MTS) at the
amino terminus that is processed in a 2-step cleavage by the mitochondrial matrix processing peptidase (MPP) as it is imported into the mitochondrial matrix. The resulting protein is a 130-amino acid, 14.2 kDa mature hFXN protein (hFXN$_{81-210}$). Sequences of the full-length hFXN and mature hFXN are shown in Table 1 below.

TABLE 1

| Sequences of the full-length hFXN and mature hFXN. | | |
| --- | --- | --- |
| SEQ ID NO. | Protein | Amino Acid Sequence |
| 1 | Full-length hFXN hFXN$_{1-210}$ | MWTLGRRAVAGLLASPSPAQAQTLTRVPRPAELAPLCGR RGLRTDIDATCTPRRASSNQRGLNQIWNVKKQSVYLMNL RKSGTLGHPGSLDETTYERLAEETLDSLAEFFEDLADKPY TFEDYDVSFGSGVLTVKLGGDLGTYVINKQTPNKQIWLS SPSSGPKRYDWTGKNWVYSHDGVSLHELLAAELTKALK TKLDLSSLAYSGKDA |
| 2 | Mature hFXN hFXN$_{81-210}$ | SGTLGHPGSLDETTYERLAEETLDSLAEFFEDLADKPYTF EDYDVSFGSGVLTVKLGGDLGTYVINKQTPNKQIWLSSP SSGPKRYDWTGKNWVYSHDGVSLHELLAAELTKALKTK LDLSSLAYSGKDA |

The full-length hFXN (SEQ ID NO: 1) comprises mature hFXN (SEQ ID NO: 2) and a mitochondrial targeting sequence (MTS) having the amino acid sequence MWTL-GRRAVAGLLASPSPAQAQTLTRVPRPAELAPLCGRR-GLRTDIDATCTPRRASS NQR-GLNQIWNVKKQSVYLMNLRK (SEQ ID NO: 3).

In some embodiments, the FXN that is measured by the methods of the present disclosure may be a mammalian FXN. In some embodiments, the FXN that is measured by the methods of the present disclosure may be a human FXN (hFXN). In some embodiments, the FXN that is measured by the methods of the present invention may be a monkey FXN, e.g., FXN from a cynomolgus macaque.

In some aspects, the FXN that is quantified by the methods provided by the present disclosure may be an endogenous FXN, i.e., FXN that is naturally present in an in vitro sample, e.g., a biological sample from a subject, or in a subject. In other aspects, the FXN that is quantified by the methods provided by the present disclosure may be an exogenous FXN, i.e., FXN that has been added to an in vitro sample, or that has been administered to a subject, e.g., and is thereby present in a biological sample from the subject. An exogenous FXN may be comprised in an FXN fusion protein, e.g., TAT-GG-FXN (SEQ ID NO: 11).

As used herein, the term "FXN fusion protein" refers to an artificial polypeptide that comprises FXN, e.g., full-length hFXN (SEQ ID NO: 1) or mature hFXN (SEQ ID NO: 2). In some embodiments, the FXN fusion protein also comprises a cell penetrating peptide (CPP).

The term "cell penetrating peptide" or "CPP", as used herein, refers to a short peptide sequence, typically between 5 and 30 amino acids long, that can facilitate cellular intake of various molecular cargo, such as proteins. Within the context of the present invention, a CPP present in an FXN fusion protein facilitates the delivery of the FXN fusion protein into a cell, e.g., a recipient cell.

CPPs may be polycationic, i.e., have an amino acid composition that either contains a high relative abundance of positively charged amino acids, such as lysine or arginine. CCPs may also be amphipathic, i.e., have sequences that contain an alternating pattern of polar/charged amino acids and non-polar, hydrophobic amino acids. CPPs may also be hydrophobic, i.e., contain only apolar residues with low net charge, or have hydrophobic amino acid groups that are crucial for cellular uptake.

A CPP that may be comprised in the FXN fusion protein useful in the context of the present invention may be any CPP known to a person skilled in the art. For example, the CPP may be any CPP listed in the Database of Cell-Penetrating Peptides CPPsite 2.0, the entire contents of which are hereby incorporated herein by reference. For examples, CPPs useful in the context of the present invention may a cell penetrating peptide derived from a protein selected from the group consisting of HIV Trans-Activator of Transcription peptide (HIV-TAT), galanin, mastoparan, transportan, penetratin, polyarginine, or VP22. In some embodiments, the CPP comprises a transduction domain of TAT protein comprising amino acids 47-57 of the 86 amino acid full length HIV-TAT protein (which 11 amino acid peptide may also be referred to herein as "HIV-TAT"; SEQ ID NO:4). In one embodiment, the CPP consists of HIV-TAT (SEQ ID NO:4). In some embodiments, the CPP comprises amino acids 47-57 of the 86 amino acid full length HIV-TAT protein with a methionine added at the amino terminus for initiation (12 AA; "HIV-TAT+M"): MYGRKKRRQRRR (SEQ ID NO: 15). Table 1 below lists amino acid sequences of exemplary CPPs.

TABLE 1

| Exemplary CPPs and corresponding sequences | | |
| --- | --- | --- |
| SEQ ID NO. | CPP | Amino Acid Sequence |
| 4 | HIV-TAT | YGRKKRRQRRR |
| 15 | HIV-TAT + M | MYGRKKRRQRRR |
| 5 | Galanin | GWTLNSAGYLLGPHAVGNHRSFSDKNGLTS |
| 6 | Mastoparan | INLKALAALAKKIL-NH$_2$ |
| 7 | Transportan | GWTLNSAGYLLGKINLKALAALAKKIL |
| 8 | Penetratin | RQIKIWFQNRRMKWKK |
| 9 | Polyarginine | RRRRRRRRR |
| 10 | VP22 | DAATATRGRSAASRPTERPRAPARSASRPR RPVE |

In some embodiments, the CPP comprised in the FXN fusion protein is HIV-TAT (SEQ ID NO: 4) or HIV-TAT+M (SEQ ID NO: 15). In some embodiments, the FXN fusion protein comprises full-length FXN, e.g., SEQ ID NO: 1, and HIV-TAT, e.g., SEQ ID NO: 4 or HIV-TAT+M (SEQ ID NO: 15), as CPP.

In some embodiments, in FXN fusion proteins of the present disclosure, the CPP may be fused together with the FXN, e.g., full-length FXN, via a linker to form a single polypeptide chain. In one embodiment, the linker may comprise the amino acid sequence GG. In one embodiment, the linker consists of the amino acid sequence GG. In some embodiments, the CPP is located at the N-terminus and the FXN is located at the C-terminus. In some embodiments, the CPP is located at the C-terminus and the FXN is located at the N-terminus. It will be appreciated that, in some embodiments, the methods provided herein may be used to detect an FXN fusion protein comprising any CPP and FXN, e.g., full-length FXN, wherein the CPP and FXN are fused via a GG linker.

In some embodiments, the FXN fusion protein comprises the following amino acid sequence (224 amino acids): MYGRKKRRQRRRGGMWTLGRRAVAGL-LASPSPAQAQTLTRVPRPAELAPLCGRRG LRTDI-DATCTPRRASSNQR-GLNQIWNVKKQSVYLMNLRKSGTLGHPGSLDETTYERL AEETLDSLAEFFEDLADKPYT-FEDYDVSFGSGVLTVKLGGDLGTYVINKQTPNKQIW LSSPSSGPKRYDWTGKNWVYSHDGVSLHELLAAEL-TKALKTKLDLSSLAYSGKDA (SEQ ID NO: 11). In some embodiments, the FXN fusion protein consists of the amino acid sequence of SEQ ID NO: 11, i.e., TAT-GG-FXN. TAT-GG-FXN is further described in U.S. Provisional Patent Application Nos. 62/891,029, the entire contents of which are hereby incorporated herein by reference.

In some aspects, the CPP, e.g., HIV-TAT, that is present in an FXN fusion protein of the present disclosure facilitates delivery of the FXN fusion protein into a cell, e.g., a cell that may be present in vitro, ex vivo, or in a subject. Once inside the cell, the FXN fusion protein may be processed by cellular machinery to remove the CPP, e.g., HIV-TAT, from the FXN. Accordingly, the term "unprocessed FXN fusion protein", as used herein, refers to an intact FXN fusion protein, i.e., the full length FXN fusion protein, or the FXN fusion protein from which CPP, e.g., HIV-TAT, has not been removed. Such an FXN fusion protein may be an FXN fusion protein that has not been delivered into a cell. For example, an unprocessed FXN fusion protein may be present in the circulation, e.g., in the plasma, of a subject following administration to the subject of the FXN fusion protein. In some embodiments, an FXN fusion protein may be an FXN fusion protein that has been delivered to a cell but has not been processed by cellular machinery to remove the CPP, e.g., HIV-TAT. In some embodiments, the unprocessed FXN fusion protein comprises the amino acid sequence of SEQ ID NO: 11. In some embodiments, the unprocessed FXN fusion protein consists of the amino acid sequence of TAT-GG-FXN (SEQ ID NO: 11).

Mass Spectrometry-Based Methods for Quantifying FXN and FXN Fusion Proteins

The present disclosure provides mass spectrometry-based methods for determining the amount of FXN or FXN fusion protein, e.g., unprocessed frataxin (FXN) fusion protein, such as TAT-GG-FXN (SEQ ID NO: 11), in a sample. In some embodiments, the sample may be an in vitro sample. In some embodiments, the sample may be a biological sample, e.g., comprising biological fluid or tissue. In some embodiments, the biological sample (e.g., comprising biological fluid or tissue) is derived from a subject, e.g., a subject with FRDA and/or a subject being administered the unprocessed FXN fusion protein.

In some aspects, the amount of FXN or FXN fusion protein in a sample determined using the methods of the present disclosure is an amount that is not normalized. In other aspects, the amount of FXN or FXN fusion protein determined using the methods of the present disclosure are normalized, e.g., normalized to the total amount of protein present in the sample. The amount of total protein present in a sample may be determined by any method known in the art for determining the amount of total protein, e.g., the BCA assay.

In some aspects, methods of the present disclosure are characterized by a high precision and accuracy of measurement of the amount of FXN or FXN fusion protein. For example, methods provided by the present invention may be characterized by a precision as measured by % coefficient of variation (% CV) of about 20% or less, e.g., about 15% or less, about 14% or less, about 13% or less, about 12% or less, about 11% or less, about 10% or less, about 9% or less, about 8% or less, about 7% or less, about 6% or less, about 5% or less, about 4% or less, about 3% or less, about 2% or less or about 1% or less. In some aspects, methods provided by the present invention may be characterized by % CV of 10% of less.

In some aspects, methods of the present disclosure may be characterized by an accuracy of about 80% to about 120%, e.g., about 80% to about 110%, or about 80% to about 100%, or about 85% to about 120%, or about 85% to about 110%, or about 85% to about 100%, or about 90% to about 120%, or about 90% to about 110%, or about 90% to about 100%, or about 95% to about 120%, or about 95% to about 110%, or about 95% to about 100%

In some aspects, methods of the present disclosure, when used to measure the amount of an FXN fusion protein, may be linear for concentrations of unprocessed FXN fusion protein ranging from about 0.250 ng/mL to about 25.000 ng/mL.

In some aspects, methods of the present disclosure, when used to measure the amount of TAT-GG-FXN (SEQ ID NO: 11), may be linear for concentrations of unprocessed TAT-GG-FXN ranging from about 0.250 ng/mL to about 25.000 ng/mL.

In some embodiments, methods of the present disclosure may comprise purifying by immunocapture FXN or FXN fusion protein present in a sample, thereby obtaining immunocaptured complexes comprising the FXN or FXN fusion protein; subjecting the immunocaptured complexes to digestion by a protease to obtain peptides derived from FXN or FXN fusion protein; and analyzing the peptides derived from FXN or FXN fusion protein by liquid chromatography and tandem mass spectrometry (LC-MS/MS) to determine the amount of FXN or FXN fusion protein present in a sample. In some embodiments, the protease may be selected from the group consisting of trypsin, chymotrypsin, LysC, LysN, AspN, GluC and ArgC. In one embodiment, the protease is trypsin.

In some aspects, methods of the present disclosure comprise detecting peptides derived from FXN or FXN fusion protein after digestion of the immunocaptured complexes with a protease, e.g., trypsin, i.e., tryptic peptides derived from FXN and/or FXN fusion protein. The tryptic peptides that may be monitored and/or quantified in the methods of the present disclosure are summarized in Table 2 below.

TABLE 2

Peptides quantified and/or monitored in the methods of the invention

| Peptide Name | Amino Acid Sequence | SEQ ID NO. | Characteristics |
|---|---|---|---|
| Linker Peptide (Peptide GGM) | GGMWTLGR | 12 | Unique to TAT-GG-FXN; Linker between TAT and MTS sequences; Not present in TAT-GG-FXN mature form |
| Peptide SGT | SGTLGHPGSLDETTYER | 13 | N-terminal peptide of the mature TAT-GG-FXN (i.e., of the mature hFXN); Not found in the monkey proteome; Surrogate peptide for TAT-GG-FXN quantitation |
| Peptide LGG | LGGDLGTYVINK | 14 | Peptide from conserved region of FXN protein; Common to both TAT-GG-FXN and cynomolgus monkey FXN; Can be used to quantify the endogenous cynomolgus monkey FXN |

In some aspects, the methods of the present invention comprise detecting and/or quantifying at least one of the peptides as listed in Table 2. In some aspects, the methods of the present invention comprise tandem mass spectrometry analysis (MS/MS). For example, in some embodiments, the linker peptide (peptide GGM) may be detected and/or quantified using MS/MS by monitoring the transition 439.2→632.3 and/or the transition 439.2→446.3. In some aspects, the peptide SGT may be detected and/or quantified using MS/MS by monitoring the transition 607.3→669.3. In some aspects, the peptide LGG may be detected and/or quantified using MS/MS by monitoring the transition 625.3→794.4.

In some aspects, the methods of the present invention may involve carrying out liquid chromatography (LC) prior to mass spectrometry. For example, the LC may be a reversed-phase LC.

In some embodiments, the methods of the present invention may involve purifying by immunocapture the unprocessed FXN fusion protein from said sample prior to MS. For example, a method of the present disclosure may comprise the following steps:

a) purifying by immunocapture the unprocessed FXN fuson protein from the sample, thereby obtaining immunocaptured complexes comprising the unprocessed FXN fusion protein;

b) subjecting said immunocaptured complexes comprising the unprocessed FXN fusion protein to digestion by a protease, e.g., trypsin, thereby producing, e.g., the peptide comprising SEQ ID NO: 12; and/or the peptide comprising SEQ ID NO: 13; and/or the peptide comprising SEQ ID NO: 14; and c) determining the amount of the peptide comprising SEQ ID NO: 12; and/or the peptide comprising SEQ ID NO: 13; and/or the peptide comprising SEQ ID NO: 14 by liquid chromatography and tandem mass spectrometry (LC/MS-MS).

In some embodiments, the peptides produced by said methods include the peptide consisting of SEQ ID NO: 12; and/or the peptide consisting of SEQ ID NO: 13; and/or the peptide consisting of SEQ ID NO: 14. In some embodiments, the amount of peptide determined by liquid chromatography and tandem mass spectrometry (LC/MS-MS) in said method include the peptide consisting of SEQ ID NO:

12; and/or the peptide consisting of SEQ ID NO: 13; and/or the peptide consisting of SEQ ID NO: 14.

In the context of the present invention, the immunocapture may be carried out using a binding protein, e.g., an antibody, comprising an antigen binding domain that specifically binds FXN or FXN fusion protein. In some embodiments, the binding protein, e.g., an antibody, comprises an antigen binding domain that specifically binds to FXN or the FXN portion of the FXN fusion protein.

In some embodiments, the binding protein, e.g., an antibody, comprises an antigen binding domain that specifically binds to the FXN fusion protein but does not bind to FXN, such as endogenous FXN present in a sample. For example, in some embodiments the binding protein, e.g., an antibody, comprises an antigen binding domain that specifically binds to a CPP present in the FXN fusion protein, such as HIV-TAT.

In some aspects, the present disclosure provides a method for determining the amount of unprocessed frataxin (FXN) fusion protein in a sample, the method comprising determining the amount of a peptide in said sample by using mass spectrometry (MS), wherein said peptide comprises the amino acid sequence GGMWTLGR (SEQ ID NO: 12); and wherein the unprocessed FXN fusion protein comprises, from N-terminus to C-terminus, a cell penetrating peptide (CPP); a mitochondrial targeting sequence (MTS) comprising SEQ ID NO: 3; and FXN comprising SEQ ID NO: 2.

In some embodiments, the CPP comprises HIV-TAT (SEQ ID NO: 4) or HIV-TAT+M (SEQ ID NO: 15). In some embodiments, the unprocessed FXN fusion protein comprises the amino acid sequence of SEQ ID NO: 11. In some embodiments, the unprocessed FXN fusion protein consists of the amino acid sequence of TAT-GG-FXN (SEQ ID NO: 11).

In some embodiments, the present disclosure provides a method for determining the amount of unprocessed TAT-GG-FXN (SEQ ID NO: 11) in a sample, the method comprising determining the amount of at least one peptide in said sample by using MS, wherein the at least one peptide is selected from the group consisting of: a) a peptide comprising or consisting of the amino acid sequence SGTLGHPGSLDETTYER (SEQ ID NO: 13); and b) a peptide comprising or consisting of the amino acid sequence LGGDLGTYVINK (SEQ ID NO: 14); wherein the method comprises purifying by immunocapture the unprocessed TAT-GG-FXN from said sample prior to MS; wherein the immunocapture is carried out using a binding protein, e.g., an antibody, comprising an antigen binding domain, wherein said antigen binding domain is capable of binding a TAT protein transduction domain. In some embodiments, the binding protein, e.g., antibody, comprises an antigen binding domain that specifically binds to TAT protein transduction domain present in TAT-GG-FXN.

In some aspects, the present disclosure provides a method for determining the amount of FXN in a tissue sample, the method comprising determining the amount of at least one peptide derived from said FXN in said sample by using MS, wherein said at least one peptide is selected from the group consisting of: a) a peptide comprising or consisting of the amino acid sequence SGTLGHPGSLDETTYER (SEQ ID NO: 13); and b) a peptide comprising or consisting of the amino acid sequence LGGDLGTYVINK (SEQ ID NO: 14); wherein the method is characterized by at least one of the following: the method has a precision as measured by % coefficient of variation (% CV) of 20% or less; and the method has an accuracy of about 80% to about 120%.

Samples for Analysis Using Methods of the Disclosure

Any sample may be used with the methods of the present disclosure to determine the amount of FXN or FXN fusion protein, e.g., TAT-GG-FXN (SEQ ID NO: 11). In some embodiments, the methods of the present disclosure are useful for analyzing the amount of FXN or FXN fusion protein in a solid sample, e.g., tissue sample, such as a buccal swab or a skin biopsy. In some embodiments, the methods of the present disclosure are useful for analyzing the amount of FXN or FXN fusion protein in a sample derived from blood and may comprise, e.g., platelets. In some embodiments, the sample may be a plasma sample.

Buccal swabs may be obtained from a subject, e.g., a mammal, e.g., a monkey or a human, by collecting buccal cells using Isohelix Swabs. The buccal swabs can be stored in frozen tubes until further use. The buccal swabs may further be processed by addition of a buffer, such as a RIPA buffer. In some embodiments, the RIPA buffer may also contain a protease inhibitor, such as EDTA free Halt™ protease inhibitor cocktail. The buccal swabs may further be vortexed and sonicated prior to immunocapture.

Skin biopsies may be obtained from a subject, e.g., a mammal, e.g., a monkey or a human, by collecting biopsy punches. The biopsy punches may be snap frozen in liquid nitrogen until further use. The skin biopsies may further be processed by mincing the skin punches into pieces, e.g., by using a surgical blade, and transferring the minced tissue to Lysing Matrix D tubes (MP Biomedicals). The skin biopsies may further be processed by addition of a buffer, such as a RIPA buffer. In some examples, the RIPA buffer may also contain a protease inhibitor, such as EDTA free Halt™ protease inhibitor cocktail. The skin biopsies may further be sonicated and homogenized, e.g., by using the FastPrep-96™ grinder. The sonication and homogenization steps may be repeated as necessary prior to immunocapture.

In some embodiments, methods of the present disclosure are particularly suitable for analyzing solid samples, e.g., tissue samples, such as buccal swabs or skin biopsies, and are characterized by higher accuracy and precision as compared to the previously described methods for determining the amount of FXN. For example, the previously described methods of determining the amount of FXN in samples, e.g., solid tissues, such as buccal swabs, were characterized by high variability.

Further, skin samples were not previously used for measuring FXN levels in a subject. The present inventors unexpectedly and surprisingly discovered that FXN may be reliably measured in skin samples. The present inventors have also unexpectedly and surprisingly discovered that levels of FXN or FXN fusion protein, such as TAT-GG-FXN (SEQ ID NO: 11), in the skin, detectably increase as a result of administration of FXN protein replacement therapy, e.g., therapy comprising administration of TAT-GG-FXN. Thus, the present inventors have discovered that skin samples, such as skin biopsies, may be used to monitor levels of FXN in a subject, e.g., following administration of FXN or FXN fusion protein, such as TAT-GG-FXN.

Accordingly, in some aspects, the present disclosure provides a method for determining the amount of FXN in a skin sample, the method comprising determining the amount of at least one peptide derived from said FXN in the skin sample by using MS, wherein the at least one peptide is selected from the group consisting of: a) a peptide comprising the amino acid sequence GGMWTLGR (SEQ ID NO: 12); b) a peptide comprising the amino acid sequence SGTLGHPGSLDETTYER (SEQ ID NO: 13); and c) a peptide comprising the amino acid sequence LGGDLGTYVINK (SEQ ID NO: 14). In some embodiments, the present disclosure provides a method for determining the amount of FXN in a skin sample, the method comprising determining the amount of at least one peptide derived from said FXN in the skin sample by using MS, wherein the at least one peptide is selected from the group consisting of: a) a peptide consisting of the amino acid sequence GGMWTLGR (SEQ ID NO: 12); b) a peptide consisting of the amino acid sequence SGTLGHPGSLDET-TYER (SEQ ID NO: 13); and c) a peptide consisting of the amino acid sequence LGGDLGTYVINK (SEQ ID NO: 14).

EXAMPLES

Example 1

The goal of this experiment was to develop an LC/MS/MS assay to determine the amount of TAT-GG-FXN (SEQ ID NO: 11) in buccal cells, skin biopsies and platelets derived from cynomolgus monkeys, following repeated administration of TAT-GG-FXN for 14 days.

Materials and Methods

Biological Samples

Preparation of biological samples used in the experiment is illustrated in FIG. 1.

Skin biopsy samples were prepared by mincing 8 mm skin punches with a scalpel and homogenizing them in RIPA buffer using a FastPrep-96 and sonication. Buccal cell samples were prepared by extracting cells scraped with a buccal swab (Isohelix SK-2S), lysing by incubation in RIPA buffer, vortexing and sonication. Platelet samples were prepared by collecting blood samples in 8.5 mL ACD tubes, isolating the platelets by centrifugation and lysing in RIPA buffer by vortexing and sonication.

Calibration standards and QCs were prepared in proxy matrix fortified with TAT-GG-FXN from 0.250 to 25.000 ng/mL. Matrix QCs were prepared in pooled tissue homogenates at low and high QC concentrations.

Total Protein Determination

Total protein concentration of each sample was determined using the Pierce™ BCA Protein Assay Kit and used for data normalization.

Sample Processing

Sample processing for hybrid LC-MS/MS analysis is illustrated in FIG. 2. TAT-GG-FXN was immunopurified using a biotinylated anti-FXN antibody. A $^{15}$N-labeled SILAC TAT-GG-FXN was used as an internal standard. Following trypsin digestion, 3 peptides as shown in the Table 4 below and corresponding $^{15}$N-labeled peptides were monitored by LC-MS/MS on a SCIEX 6500+.

TABLE 4

Peptides monitored for TAT-GG-FXN quantitation

| Peptide Name | Amino Acid Sequence | SEQ ID NO. | Characteristics |
|---|---|---|---|
| Linker Peptide (Peptide GGM) | GGMWTLGR | 12 | Unique to TAT-GG-FXN<br>Linker between TAT and MTS sequences<br>Not present in TAT-GG-FXN mature form<br>Monitored for informative purpose |
| Peptide SGT | SGTLGHPGSLDETTYER | 13 | N-terminal peptide of the mature TAT-GG-FXN<br>Not found in the monkey proteome<br>Surrogate peptide for TAT-GG-FXN quantitation |
| Peptide LGG | LGGDLGTYVINK | 14 | Peptide from conserved region of FXN protein<br>Common to both TAT-GG-FXN and cynomolgus monkey FXN<br>Can be used to quantify the endogenous cynomolgus monkey FXN<br>Monitored for informative purpose |

Processing of Results

Peak area ratios of TAT-GG-FXN derived tryptic peptides and their corresponding $^{15}$N-labeled peptides were used to construct calibration curves (weighted $1/x^2$ linear regression).

The concentration of TAT-GG-FXN in samples was determined (in ng/mL) using the calibration curve equation. After normalization using total protein concentration (μg protein per mL of homogenate), the TAT-GG-FXN concentrations are reported as μg of TAT-GG-FXN per μg of total protein.

Results

Shown in Table 5 below are the results of TAT-GG-FXN measurements in buccal cells, skin biopsies and platelets. Also shown in Table 5 are the precision and accuracy (multi-peptide) of the assay.

TABLE 5

TAT-GG-FXN precision and accuracy (multi-peptide) in buccal cells, skin biopsies and platelets.

| Peptide | Sample Type | | Nominal Concentration (ng/mL) | Accuracy | % CV (N = 3) | Code |
|---|---|---|---|---|---|---|
| Linker Peptide (Peptide GGM) | Buccal Cells | Low QC | 0.750 | 97.4 | 2.3 | |
| | | High QC | 18.750 | 101.9 | 1.3 | |
| | Skin Biopsies | Low QC | 0.750 | 99.7 | 8.0 | |
| | | High QC | 18.750 | 104.5 | 4.6 | |
| | Platelets | Low QC | 0.750 | 97.5 | 11.1 | |
| | | High QC | 18.750 | 106.4 | 4.4 | |
| Peptide SGT | Buccal Cells | Low QC | 0.750 | 84.4 | 4.3 | |
| | | High QC | 18.750 | 102.6 | 1.2 | |
| | Skin Biopsies | Low QC | 0.750 | 87.8 | 9.0 | |
| | | High QC | 18.750 | 107.1 | 3.1 | |
| | Platelets | Low QC | 0.750 | 92.7 | 7.1 | |
| | | High QC | 18.750 | 107.3 | 2.5 | |
| Peptide LGG | Buccal Cells | Endogenous | 4.869* | 100.0 | 3.2 | |
| | | Low QC | 5.619** | 95.6 | 3.7 | |
| | | High QC | 23.619** | 102.0 | 2.2 | |
| | Skin Biopsies | Endogenous | 10.153* | 100.0 | 5.0 | |
| | | Low QC | 10.903** | 99.4 | 2.8 | |
| | | High QC | 28.903** | 104.4 | 2.3 | >ULOQ |

TABLE 5-continued

| | | TAT-GG-FXN precision and accuracy (multi-peptide) in buccal cells, skin biopsies and platelets. | | | |
|---|---|---|---|---|---|
| Peptide | Sample Type | Nominal Concentration (ng/mL) | Accuracy | % CV (N = 3) | Code |
| Platelets | Endogenous | 19.867* | 100.0 | 2.2 | |
| | Low QC | 20.617** | 94.5 | 3.8 | |
| | High QC | 38.617** | 104.1 | 1.1 | >ULOQ |

>ULOQ: Above upper limit of quantitation. Extrapolated values are presented.
*Back-calculated endogenous level. Average of 3 replicates.
**Endogenous level + spiked-in TAT-GG-FXN at low and high QC levels.

Figure 3:
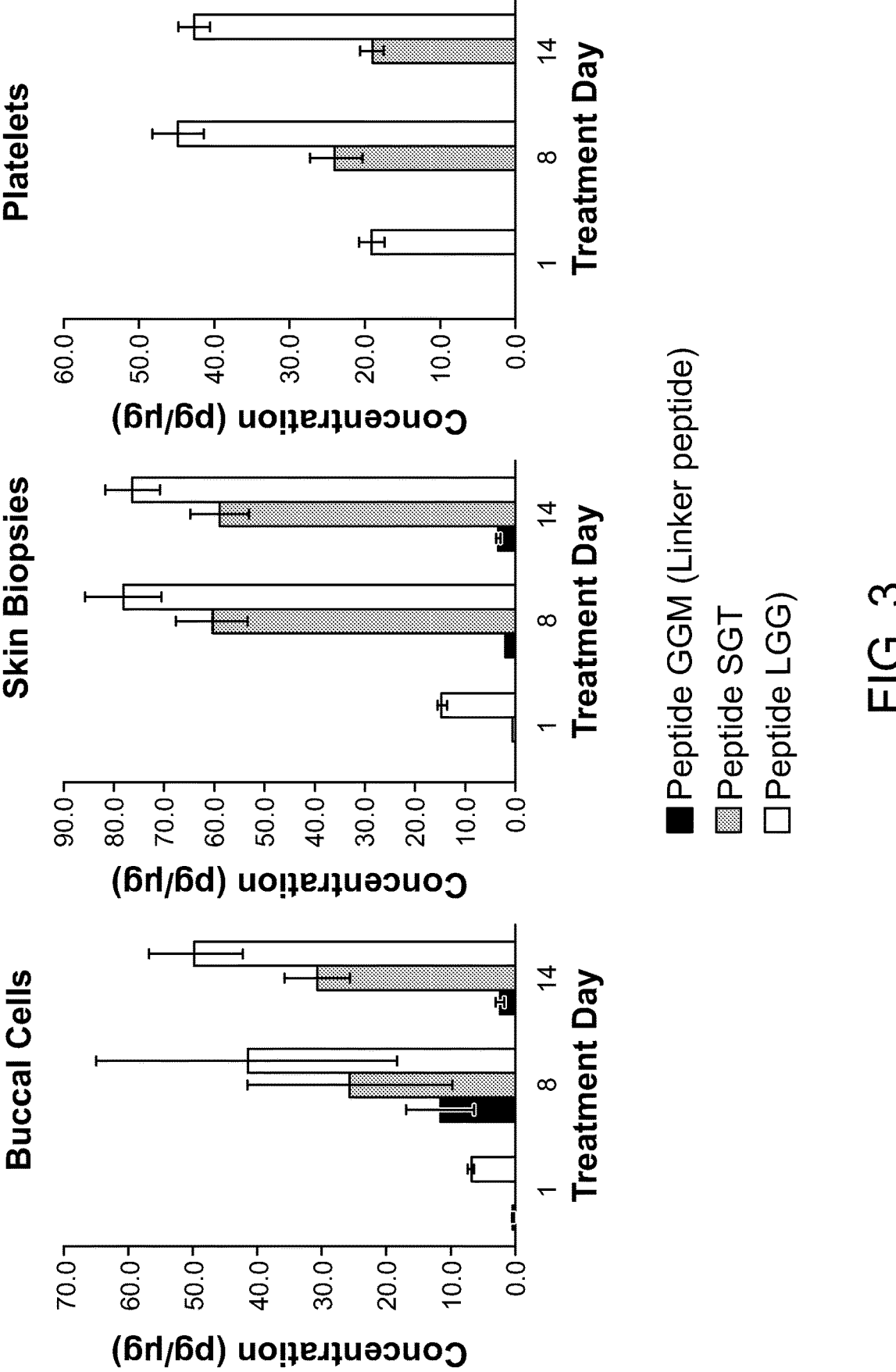
FIG. 3 is a series of graphs showing the concentration of
TAT-GG-FXN (SEQ ID NO: 11) levels in monkey tissues
(N=6) following repeated subcutaneous (SC) administration
at 15 mg/kg BID for 14 days. Data is expressed at pg of
TAT-GG-FXN per µg of total protein.

FIG. 3 is a series of graphs showing the concentration of TAT-GG-FXN levels in monkey tissues (N=6) following repeated subcutaneous (SC) administration at 15 mg/kg BID for 14 days. Data is expressed at pg of TAT-GG-FXN per µg of total protein.

Figure 4:
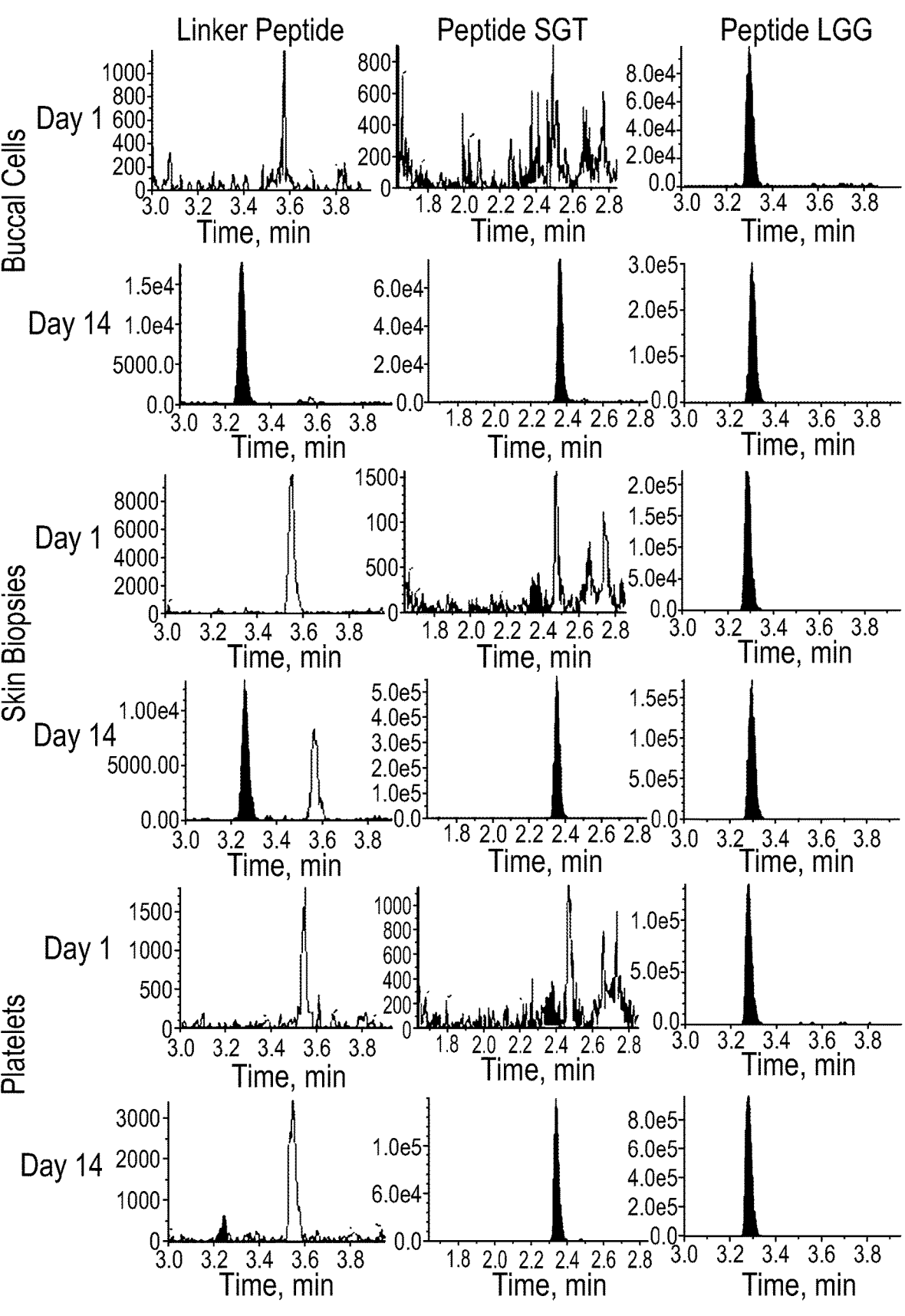
FIG. 4 is a series of representative chromatograms of
TAT-GG-FXN tryptic peptides in monkey tissues prior to
dosing (Day 1) and following repeated SC administration at
15 mg/kg BID for 14 days.

FIG. 4 is a series of representative chromatograms of TAT-GG-FXN tryptic peptides in monkey tissues prior to dosing (Day 1) and following repeated SC administration at 15 mg/kg BID for 14 days.

CONCLUSIONS

The results from the studies provided in this Example indicate that, following repeated administration of TAT-GG-FXN (SEQ ID NO: 11) for 14 days, TAT-GG-FXN not only accumulates in the tissues outside of the systemic circulation but also is predominantly present as the mature FXN protein. The results from this study illustrate how hybrid LC-MS/MS assays can be used to simultaneously gain insight into the concentration, disposition and processing of biotherapeutics, and in particular, of TAT-GG-FXN.

The invention claimed is:

1. A method for determining the amount of unprocessed frataxin (FXN) fusion protein in a sample, said method comprising determining the amount of at least one peptide in said sample by using mass spectrometry (MS), wherein said unprocessed FXN fusion protein comprises full length FXN having the sequence of SEQ ID NO: 1 and a cell penetrating peptide (CPP) selected from HIV-TAT having the sequence of SEQ ID NO: 4 and HIV-TAT+M having the sequence of SEQ ID NO: 15;

wherein said at least one peptide is selected from the group consisting of:

a) a peptide comprising the amino acid sequence SGTLGHPGSLDETTYER (SEQ ID NO: 13); and b) a peptide comprising the amino acid sequence LGGDLGTYVINK (SEQ ID NO: 14);

wherein said method comprises purifying by immunocapture the unprocessed FXN fusion protein from said sample prior to MS;

wherein said immunocapture is carried out using a binding protein comprising an antigen binding domain, wherein said binding protein is capable of binding a TAT protein transduction domain.

2. The method of claim 1, wherein said sample is obtained from a subject being administered the unprocessed FXN fusion protein.

3. The method of claim 1, wherein said method comprises the following steps:

a) purifying by immunocapture the unprocessed FXN fusion protein from said sample, thereby obtaining immunocaptured complexes comprising the unprocessed FXN fusion protein;

b) subjecting said immunocaptured complexes comprising the unprocessed FXN fusion protein to digestion by trypsin, thereby producing the peptide comprising SEQ ID NO: 13 and/or the peptide comprising SEQ ID NO: 14; and c) determining the amount of the peptide comprising SEQ ID NO: 13 and/or the peptide comprising SEQ ID NO: 14 by liquid chromatography and tandem mass spectrometry (LC/MS-MS).

4. The method of claim 3, wherein the MS-MS comprises monitoring the transition 607.3→669.3 for the peptide comprising SEQ ID NO: 13 and the transition 625.3→794.4 for the peptide comprising SEQ ID NO: 14.

5. The method of claim 1, wherein the sample is a tissue sample.

6. The method of claim 5, wherein the tissue sample comprises a buccal swab or a skin biopsy.

7. The method of claim 1, wherein the sample is derived from the blood of the subject.

8. The method of claim 7, wherein the sample comprises platelets or wherein the sample is a plasma sample.

9. The method of claim 1, wherein the method has a precision as measured by % coefficient of variation (% CV) of 20% or less and/or wherein the method has an accuracy of about 80% to about 120%; and/or wherein the method is linear for concentrations of unprocessed FXN fusion protein ranging from about 0.250 ng/mL to about 25.000 ng/mL.

10. The method of claim 1, wherein said unprocessed FXN fusion protein is TAT-GG-FXN (SEQ ID NO: 11).

11. A method for determining the amount of frataxin (FXN) in a tissue sample, said method comprising determining the amount of at least one peptide derived from said FXN in said sample by using Mass Spectrometry (MS), wherein said at least one peptide is selected from the group consisting of:

a) a peptide comprising the amino acid sequence SGTLGHPGSLDETTYER (SEQ ID NO: 13); and b) a peptide comprising the amino acid sequence LGGDLGTYVINK (SEQ ID NO: 14);

wherein the method is characterized by at least one of the following:

the method has a precision as measured by % coefficient of variation (% CV) of 20% or less; and the method has an accuracy of about 80% to about 120%.

12. The method of claim 11, wherein said tissue sample comprises a buccal swab or a skin biopsy.

13. The method of claim 11, wherein said tissue sample is obtained from a subject.

14. The method of claim 13, wherein said subject is being administered an FXN fusion protein.

15. The method of claim 14, wherein said FXN fusion protein comprises full length FXN having the sequence of SEQ ID NO: 1 and a cell penetrating peptide (CPP) selected from HIV-TAT having the sequence of SEQ ID NO: 4 and HIV-TAT+M having the sequence of SEQ ID NO: 15.

16. The method of claim 15, wherein said FXN fusion protein is TAT-GG-FXN (SEQ ID NO: 11).

17. The method of claim 11, wherein said method comprises the following steps:

a) purifying by immunocapture the FXN from said tissue sample, thereby obtaining immunocaptured complexes comprising FXN;

b) subjecting said immunocaptured complexes comprising FXN to digestion by trypsin, thereby producing the peptide comprising SEQ ID NO: 13 and/or the peptide comprising SEQ ID NO: 14; and c) determining the amount of the peptide comprising SEQ ID NO: 13 and/or the peptide comprising SEQ ID NO: 14 by liquid chromatography and tandem mass spectrometry (LC/MS-MS).

18. The method of claim 17, wherein the MS-MS comprises monitoring the transition 607.3→669.3 for the peptide comprising SEQ ID NO: 13 and the transition 625.3→794.4 for the peptide comprising SEQ ID NO: 14.

* * * * *

```
                         SEQUENCE LISTING

<160> NUMBER OF SEQ ID NOS: 15

<210> SEQ ID NO 1
<211> LENGTH: 210
<212> TYPE: PRT
<213> ORGANISM: Homo sapiens

<400> SEQUENCE: 1

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175
```

-continued

```
His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
        195                 200                 205

Asp Ala
    210

<210> SEQ ID NO 2
<211> LENGTH: 130
<212> TYPE: PRT
<213> ORGANISM: Homo sapiens

<400> SEQUENCE: 2

Ser Gly Thr Leu Gly His Pro Gly Ser Leu Asp Glu Thr Thr Tyr Glu
1               5                   10                  15

Arg Leu Ala Glu Glu Thr Leu Asp Ser Leu Ala Glu Phe Phe Glu Asp
            20                  25                  30

Leu Ala Asp Lys Pro Tyr Thr Phe Glu Asp Tyr Asp Val Ser Phe Gly
        35                  40                  45

Ser Gly Val Leu Thr Val Lys Leu Gly Gly Asp Leu Gly Thr Tyr Val
    50                  55                  60

Ile Asn Lys Gln Thr Pro Asn Lys Gln Ile Trp Leu Ser Ser Pro Ser
65                  70                  75                  80

Ser Gly Pro Lys Arg Tyr Asp Trp Thr Gly Lys Asn Trp Val Tyr Ser
                85                  90                  95

His Asp Gly Val Ser Leu His Glu Leu Leu Ala Ala Glu Leu Thr Lys
            100                 105                 110

Ala Leu Lys Thr Lys Leu Asp Leu Ser Ser Leu Ala Tyr Ser Gly Lys
        115                 120                 125

Asp Ala
    130

<210> SEQ ID NO 3
<211> LENGTH: 80
<212> TYPE: PRT
<213> ORGANISM: Homo sapiens

<400> SEQUENCE: 3

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4
```

```
Tyr Gly Arg Lys Lys Arg Arg Gln Arg Arg Arg
1               5                   10
```

<210> SEQ ID NO 5
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

```
Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
            20                  25                  30
```

<210> SEQ ID NO 6
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

```
Ile Asn Leu Lys Ala Leu Ala Ala Leu Ala Lys Lys Ile Leu
1               5                   10
```

<210> SEQ ID NO 7
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 8
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

```
Arg Gln Ile Lys Ile Trp Phe Gln Asn Arg Arg Met Lys Trp Lys Lys
1               5                   10                  15
```

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 9

Arg Arg Arg Arg Arg Arg Arg Arg Arg
1               5

<210> SEQ ID NO 10
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 11
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Tyr Gly Arg Lys Lys Arg Arg Gln Arg Arg Arg Gly Gly Met Trp
1               5                   10                  15

Thr Leu Gly Arg Arg Ala Val Ala Gly Leu Leu Ala Ser Pro Ser Pro
            20                  25                  30

Ala Gln Ala Gln Thr Leu Thr Arg Val Pro Arg Pro Ala Glu Leu Ala
        35                  40                  45

Pro Leu Cys Gly Arg Arg Gly Leu Arg Thr Asp Ile Asp Ala Thr Cys
    50                  55                  60

Thr Pro Arg Arg Ala Ser Ser Asn Gln Arg Gly Leu Asn Gln Ile Trp
65                  70                  75                  80

Asn Val Lys Lys Gln Ser Val Tyr Leu Met Asn Leu Arg Lys Ser Gly
            85                  90                  95

Thr Leu Gly His Pro Gly Ser Leu Asp Glu Thr Thr Tyr Glu Arg Leu
            100                 105                 110

Ala Glu Glu Thr Leu Asp Ser Leu Ala Glu Phe Phe Glu Asp Leu Ala
        115                 120                 125

Asp Lys Pro Tyr Thr Phe Glu Asp Tyr Asp Val Ser Phe Gly Ser Gly
        130                 135                 140

Val Leu Thr Val Lys Leu Gly Gly Asp Leu Gly Thr Tyr Val Ile Asn
145                 150                 155                 160

Lys Gln Thr Pro Asn Lys Gln Ile Trp Leu Ser Ser Pro Ser Ser Gly
            165                 170                 175

Pro Lys Arg Tyr Asp Trp Thr Gly Lys Asn Trp Val Tyr Ser His Asp
            180                 185                 190

Gly Val Ser Leu His Glu Leu Leu Ala Ala Glu Leu Thr Lys Ala Leu
        195                 200                 205

Lys Thr Lys Leu Asp Leu Ser Ser Leu Ala Tyr Ser Gly Lys Asp Ala
    210                 215                 220
```

```
<210> SEQ ID NO 12
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Gly Met Trp Thr Leu Gly Arg
1               5

<210> SEQ ID NO 13
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Gly Thr Leu Gly His Pro Gly Ser Leu Asp Glu Thr Thr Tyr Glu
1               5                   10                  15

Arg

<210> SEQ ID NO 14
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Leu Gly Gly Asp Leu Gly Thr Tyr Val Ile Asn Lys
1               5                   10

<210> SEQ ID NO 15
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Met Tyr Gly Arg Lys Lys Arg Arg Gln Arg Arg Arg
1               5                   10
```